United States Patent
Lee

(10) Patent No.: US 7,632,226 B2
(45) Date of Patent: Dec. 15, 2009

(54) METHOD OF MODULATING HUMAN MERIDIAN SYSTEM USING SMALL BAR MAGNET

(75) Inventor: Hong-Jae Lee, 2-102 Hanyang Apartment 1-cha, 388-33 Ssangmun-dong, Dobong-gu, Seoul (KR) 132-030

(73) Assignee: Hong-Jae Lee, Seoul (KR)

( * ) Notice: Subject to any disclaimer, the term of this patent is extended or adjusted under 35 U.S.C. 154(b) by 437 days.

(21) Appl. No.: 10/521,357

(22) PCT Filed: Jul. 10, 2003

(86) PCT No.: PCT/KR03/01366

§ 371 (c)(1),
(2), (4) Date: Jan. 14, 2005

(87) PCT Pub. No.: WO2004/011094

PCT Pub. Date: Feb. 5, 2004

(65) Prior Publication Data

US 2006/0122455 A1    Jun. 8, 2006

(30) Foreign Application Priority Data

Jul. 25, 2002    (KR) .................... 10-2002-0043764

(51) Int. Cl.
*A61N 1/00* (2006.01)
(52) U.S. Cl. ....................................................... 600/15

(58) Field of Classification Search ............... 600/1–15; 607/100; 2/159–160, 161.7, 163; 606/189; 128/898
See application file for complete search history.

(56) References Cited

U.S. PATENT DOCUMENTS

| 5,448,777 | A | * | 9/1995 | Lew | 2/161.7 |
| 5,720,046 | A | * | 2/1998 | Lopez et al. | 2/159 |
| 7,150,710 | B2 | * | 12/2006 | Haber et al. | 600/9 |
| 2002/0169357 | A1 | * | 11/2002 | Chen | 600/15 |
| 2003/0009077 | A1 | * | 1/2003 | Woo | 600/15 |

FOREIGN PATENT DOCUMENTS

| JP | 2000-325488 | 11/2000 |
| KR | 2004-6618 | 1/2004 |
| KR | 2004-52562 | 6/2004 |

* cited by examiner

*Primary Examiner*—John P Lacyk
(74) *Attorney, Agent, or Firm*—Jason Y. Pahng

(57) ABSTRACT

A method of modulating the human meridian system using a small bar magnet is provided. In the method of modulating the human meridian system, the small bar magnet has a length of 3 cm or less and a coercivity of 1000 gauss or greater. The meridian system is modulated by attaching the small bar magnet to the skin or hypodermically implanting the small bar magnet, such that the direction of flow of a magnetic force of the magnet is the same as or opposite to the direction of flow of the meridian system. The method, which can replace traditional acupuncture and/or moxibustion for modulating the human meridian system, allows ordinary people to use the same in a risk-free, safe and simple manner without causing pain to a body.

16 Claims, 5 Drawing Sheets

METHOD OF MODULATING HUMAN MERIDIAN SYSTEM USING SMALL BAR MAGNET

TECHNICAL FIELD

The present invention relates to a method of modulating the human meridian system using a small bar magnet, and more particularly, to a method of modulating the human meridian system by attaching a small bar magnet having a length of 3 cm or less, preferably 1 cm or less, to the surface of the skin of a body or by hypodermically implanting the small bar magnet, such that the direction of flow of a magnetic force of the magnet is the same as or opposite to the direction of flow of the meridian system.

BACKGROUND ART

In the oriental medical art, it is said that there are the five viscera and the six entrails in a human body and when they are harmonized, the human health is ensured, and when disharmonized, various diseases may attack. Energy circulation pathways running through a body vertically up and down, that is, from the head to legs and from the chest to arms, termed meridians, control functions of the viscera and the entrails. According to the ancient Chinese theory concerning the viscera and the entrails, the viscera include liver, heart, spleen, lung, kidney and heart constrictor, and the entrails include gall bladder, small intestine, paunch, large intestine, bladder and triple warmers. Accordingly, there are twelve main meridians named after corresponding parts of organs of the body and eight extra meridians. Among the eight extra meridians, two extra meridians passing through the front nerve center and the rear nerve center are grouped with the twelve main meridians and categorized as 14 meridians. In particular, there are points of the meridians at which the flow of an energy force, called Qi, is strong, which are called acupuncture points. The acupuncture points of each meridian are selectively stimulated by a Bosa method which is an acupuncture method combining Bo method and Sa method wherein Bo means promotive and Sa means inhibitive, to regulate an energy force, thereby promoting the flow of the energy force and harmonizing the viscera and the entrails. The acupuncture points are distributed along 14 main meridians at 360 positions throughout the body.

The ancient Chinese theory concerning the viscera and the entrails is essentially employed for determination and treatment of diseases in the clinical practice of the modern Oriental medical art. The clinical study of the modern medical science also proved that when there is abnormality in the organs or intestines, symptoms of pains, ache, stiffness, feeling of cold, hot feeling and so on, are developed in the shape of dots, lumps or lines on the skin or muscles directly associated with the abnormal organs or intestines. This phenomenon occurs just as the body is banded in a loop or knot. Also, there are several spots of strong reactivity along the band. In many cases, the spots correspond to acupuncture points.

In the Oriental medical art, acupuncture or moxibustion has been traditionally adopted to treat and regulate malfunctions of the viscera and the entrails by stimulating the acupuncture points. However, since the acupuncture or moxibustion causes severe pain arising due to bleeding, bruise or burning of the skin, people are basically unwilling to get treatment by the acupuncture or moxibustion. Thus, in spite of therapeutic effectiveness, acupuncture or moxibustion tends to be often avoided. Nowadays, infection with contagious diseases such as AIDS is a matter of great concern. The present invention relates to a method of modulating the human meridian system using a small bar magnet having a length of 3 cm or less, preferably 1 cm or less, instead of the conventional acupuncture or moxibustion.

In a conventional method of modulating the human acupuncture points or meridian system using a magnet, as shown in FIGS. 2A and 2B, either the N or S pole of a conical magnet is attached to the skin so that the magnetic field is applied to the body, thereby stimulating the acupuncture points of the body. According to the method of attaching a pole of a magnet to the skin, however, local spots with the magnet attached thereto can only be stimulated, but the effect of modulating the meridian system cannot be expected.

An example of the conventional technique is a method of stimulating acupuncture points using two magnets such that the two magnets are adhered to each other by an adhesive tape with opposite polarities contacting each other and the magnets are contacted to acupuncture points, as disclosed in Korean Patent Publication 1995-31128. Korean Patent Publication No. 1990-14007 discloses a method of activating acupuncture point of a body using an acupuncture point controller having two magnet fixing devices by arranging outer ends of a permanent magnet with N and S poles of conical magnets being differently fixed to each outer end of the permanent magnet and making the outer ends get closer to acupuncture points, thereby directing a magnetic force generated from the magnet toward acupuncture points of the body and increasing the magnetic force through an iron plate flowing from a N pole to a S pole, to supply the magnetic force to hemoglobin in blood, thereby activating acupuncture point of the body.

As a further improvement, Korean Utility Model No. 164711 discloses a method in which a large tubular magnet and a small disc-shaped magnet having pores are superposed vertically to then be housed in a synthetic resin case, and the magnets are attached to an inductive iron plate so that the small magnet is made to fixedly contact an acupuncture point to stimulate the magnetic force, thereby regulating flow of Qi of a body. Also, in the disclosed method, the magnet is attached to two different acupuncture points and N and S poles are differently contacted to the acupuncture points considering the direction of flow of an energy acting therebetween. Blood circulation is affected by a magnetic energy applied between the two acupuncture points, and the inductive iron plate serves as an antenna. According to this technique, like in the conventional technology in which acupuncture points are stimulated by infiltrating a magnetic force into parts corresponding the acupuncture points, blood circulation is promoted or inhibited using a magnetic force, based on the fact that hemoglobin in blood is ferroelectric. However, it is very difficult to apply this technique into actual practice because a device according to this technique is complicated and is inconvenient to carry.

DISCLOSURE OF THE INVENTION

To overcome the disadvantages of the conventional acupuncture and/or moxibustion for modulating the human meridian system, the inventor of the present invention conducted research into a method which can replace the conventional acupuncture and/or moxibustion for a long time and completed the present invention based on the conclusions that the same magnetic force of a bar magnet is maintained when it is attached to the surface of the skin so as to lean to the skin and when it is hypodermically implanted and that flow of the magnetic force affects the human meridian system.

The present invention provides a method of modulating the human meridian system using a small bar magnet having a length of 3 cm or less, preferably 1 cm or less, instead of conventional acupuncture or moxibustion. In the present invention, for an inactive meridian, a small bar magnet is attached to the surface of the skin or is hypodermically implanted, such that the direction of flow of a magnetic force, that is, the direction of an internal magnetic force of the magnet, is the same as the direction of flow of the meridian system, thereby promoting the human meridian system. Conversely, a small bar magnet is attached to the surface of the skin or is hypodermically implanted, such that the direction of flow of a magnetic force is opposite to the direction of flow of the meridian system, thereby inhibiting the human meridian system. In such a manner, the human meridian system is modulated using flow of a magnetic force, rather than using the conventional acupuncture.

BEST MODE FOR CARRYING OUT THE INVENTION

The present invention provides a method of modulating the human meridian system using a small bar magnet having a length of 3 cm or less and a coercivity of 1000 gauss or greater, wherein the human meridian system is promoted by attaching the small bar magnet to the skin such that such that the direction of flow of a magnetic force of the magnet is the same as the direction of flow of the meridian system, or the human meridian system is inhibited by attaching the small bar magnet to the skin such that the direction of flow of a magnetic force of the bar magnet is opposite to the direction of flow of the meridian system.

The present invention also provides a method of modulating the human meridian system using a small bar magnet having a length of 3 cm or less and a coercivity of 1000 gauss or greater, wherein the meridian system is promoted by hypodermically implanting the small bar magnet such that the direction of an internal magnetic force of the magnet is the same as the direction of flow of the meridian system, or the meridian system is inhibited by hypodermically implanting the small bar magnet such that the direction of an internal magnetic force of the magnet is opposite to the direction of flow of the meridian system.

Figure 1A:
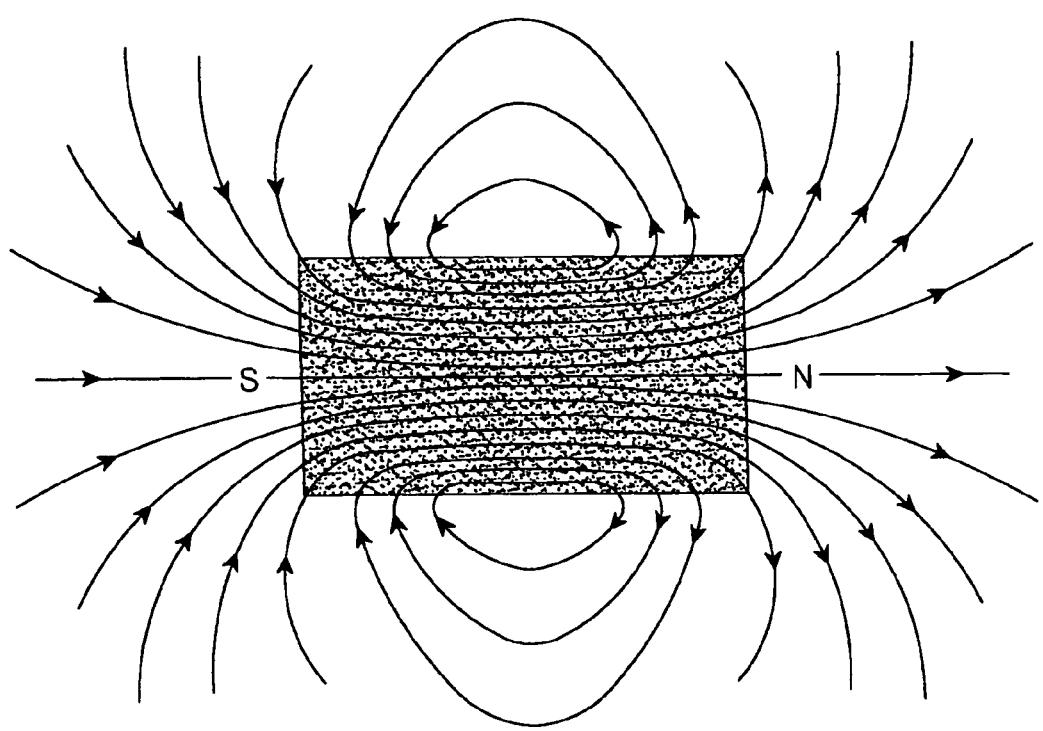
FIG. 1a shows a direction of a magnetic force of a bar magnet.
Figure 1B:
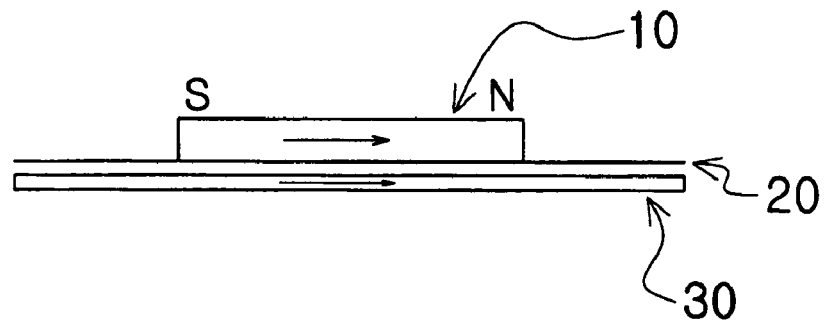
FIG. 1b shows a direction of a magnetic force of a bar magnet when the bar magnet is attached to the surface of a body in the same direction as the flow of the meridian system.
Figure 1C:
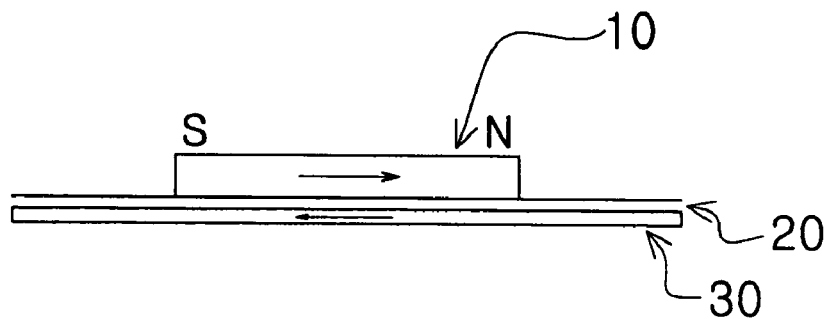
FIG. 1c shows a direction of a magnetic force of a bar magnet when the bar magnet is attached to the surface of a body in the opposite direction to the flow of the meridian system.
Figure 1D:
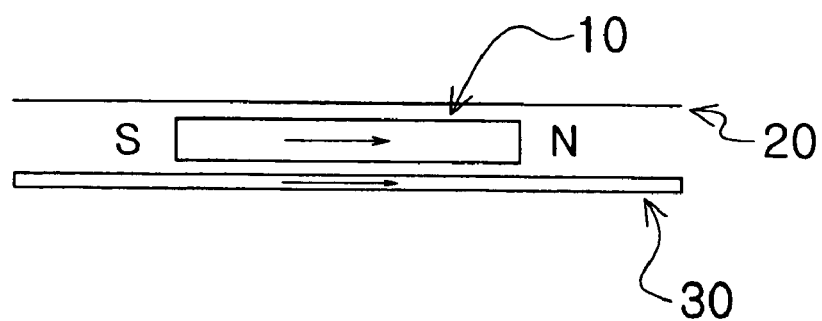
FIG. 1d shows a direction of a magnetic force of a bar magnet when the bar magnet is hypodermically implanted in the same direction as the flow of the meridian system.
Figure 1E:
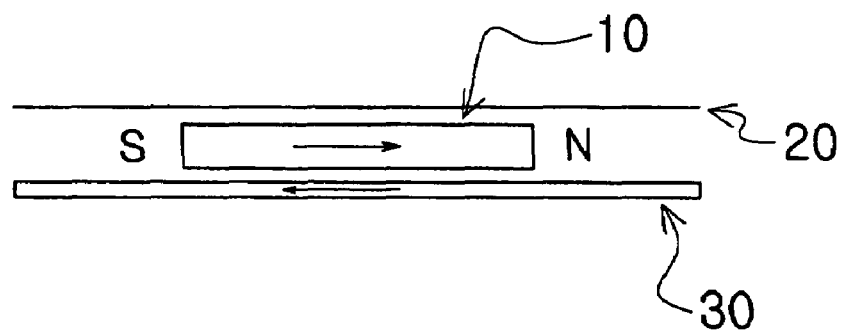
FIG. 1e shows a direction of a magnetic force of a bar magnet when the bar magnet is hypodermically implanted in the opposite direction to the flow of the meridian system.
Figure 2A:
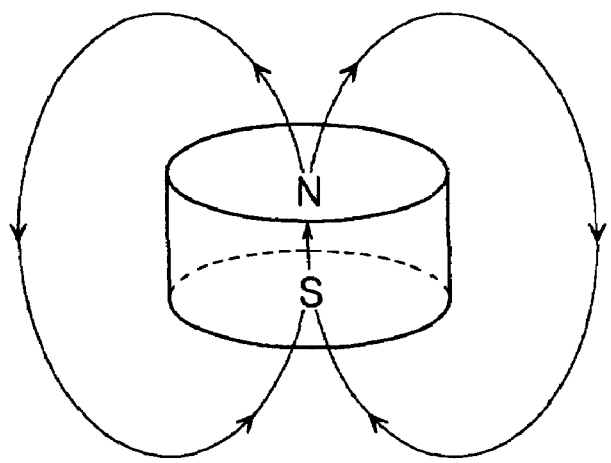
FIG. 2a shows the direction of a magnetic force of a conventional conical magnet.
Figure 2B:
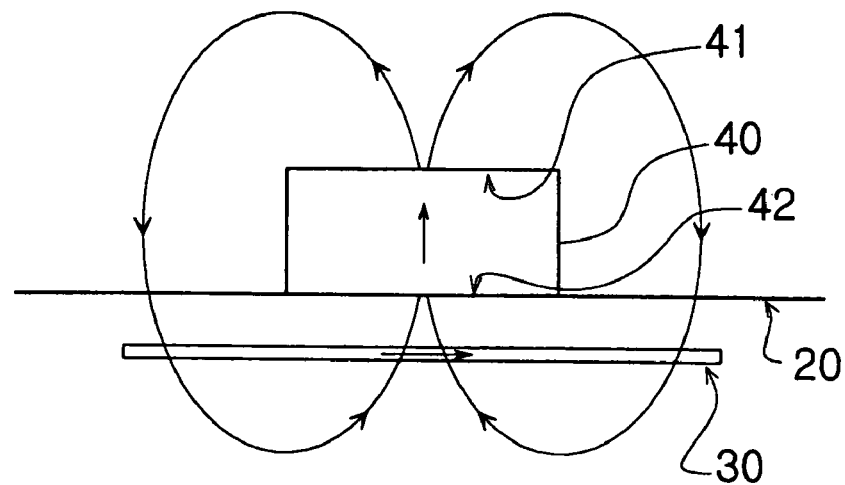
FIG. 2b shows the direction of a magnetic force and the direction of flow of the meridian system when the conventional conical magnet is attached to the surface of the skin of a body.

FIG. 1A shows a direction of a magnetic force of a small bar magnet used in the present invention. As shown in FIG. 1A, the magnetic force of the bar magnet flows from the N pole to the S pole, and polarity is directed from the S pole to the N pole inside the bar magnet. As shown in FIGS. 1B through 1E, the flow of the magnetic force is maintained in the same direction when the bar magnet is attached to the surface of a body such that it contacts the surface and when it is hypodermically implanted. According to the direction of polarity of a bar magnet attached to the body, as shown in FIGS. 1B and 1D, the direction of the magnetic force of the small bar magnet can be made to be the same as the direction of flow of the meridian system, that is, the human energy circulation system. Alternatively, as shown in FIGS. 1C and 1E, the direction of the magnetic force of the small bar magnet can be made to be opposite to the direction of flow of the meridian system.

The flow of the meridian system and a method of using the small bar magnet according to the present invention will now be described in more detail.

The human meridian system and flow thereof are described in Section <Miraculous Pivot> of <Huangdi's Internal Classic>, a classic of traditional acupuncture, which was presumably written approximately 2000 years ago in ancient China. According to this literature as cited in <Chinese Acupuncture and Moxibustion> published by Foreign Languages Press, Beijing, in 1987 and 1990, there are 12 meridians and flow of Qi is maintained in a predetermined direction along these meridians. Among the 12 meridians, six upstream meridians run through the front part of a body, that is, the chest and abdominal regions, and interior sides of the legs and arms. In other words, the six upstream meridians include the liver, kidney and spleen meridians running from the tiptoes to the chest and the lung, heart constrictor and heart meridians running from the chest to the fingertips, all running upward from the feet to the chest and from the chest to the fingertips.

On the other hand, six downstream meridians run through a body downward, including three hand-ward, outward meridians, that is, the large intestine, triple warmer and small intestine meridians running from the back of the hand to the face via the shoulder, and three foot-ward, inward meridians, that is, the stomach, gall bladder and bladder meridians running from the face, head or neck to the toes via the waist, the hip and the side and back of the leg.

As described above, the upstream meridians run from a lower part to an upper part of a body and the downstream meridians run from an upper part to a lower part of a body. Also, a magnetic force of a bar magnet flows from the N pole to the S pole and an internal magnetic force of the magnet flows from the S pole to the N pole.

As described above, the present invention is based on the fact that both the human meridian system and a magnetic force of a magnet have directionality. Based on the confirmation that when the direction of flow of a magnetic force is the same as or opposite to the direction of flow of the meridian system, the flow of the magnetic force exerts the same effect on the human meridian system as the conventional acupuncture or moxibustion, the present invention provides a new method of modulating the human meridian system using a bar magnet which can replace acupuncture or moxibustion.

In the traditional acupuncture of the oriental medical art, an acupuncture needle is inserted in the same direction as the direction of flow of the meridian system for stimulation, thereby promoting Qi, that is, the flow of an energy force, which is called a Bo (promotive) method. The Bo (promotive) method is used when physical strength is exhausted or the flow of meridians is depressed.

On the contrary, the flow of the meridian system may be overly stimulated, causing an excited state of the internal organs associated with the meridian system, which is called a robust symptom in the oriental medical art. In this case, an acupuncture needle is inserted in a direction opposite to the direction of flow of the meridian system, thereby inhibiting the flow of the meridian system, which is called a Sa (inhibitive) method.

In this case, according to the Bo (promotive) method, a tip of the acupuncture needle is inserted in the same direction as that of flow of the meridian system. According to the Sa (inhibitive) method, the tip of the acupuncture needle is opposite to the direction of flow of the meridian system.

In the present invention, the Bosa method of the traditional acupuncture are applied to a magnet, in which the direction of an acupuncture needle tip inserted into an acupuncture point is made to correspond to the direction of flow of a magnetic force. In other words, a bar magnet is attached to the surface of the skin such that the direction of an internal magnetic force of the magnet is the same as the direction of flow of the meridian system, thereby promoting the human meridian system. Conversely, the bar magnet is attached to the surface of the skin such that the direction of flow of a magnetic force is opposite to the direction of flow of the meridian system, thereby inhibiting the human meridian system. In such a manner, the human meridian system is modulated by flow of a magnetic force, rather than using conventional acupuncture.

Figure 3:
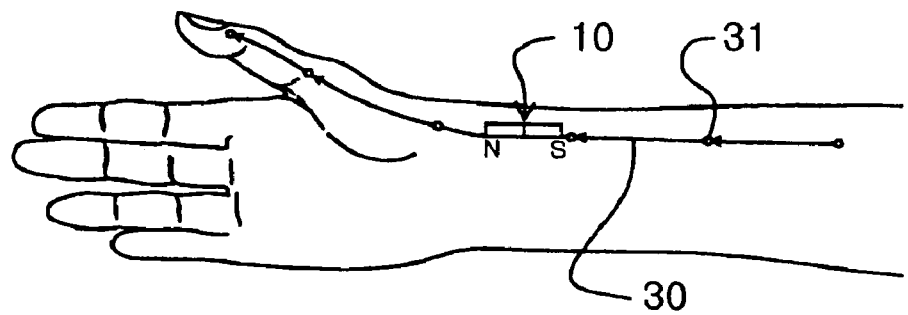
FIG. 3 shows an example in which a bar magnet is attached such that the direction of flow of a magnetic force is the same as the direction of flow of the meridian system in the lung, heart constrictor and heart meridians.

For example, as shown in FIG. 3, in the case of the human meridian system in the lung, heart constrictor and heart meridians, running from the chest to the fingertips, a bar magnet is attached such that the S pole is directed to the shoulder and the N pole is directed to the fingertips so that the direction of flow of a magnetic force is the same as the direction of flow of the meridian system, thereby promoting the human meridian system.

Figure 4:
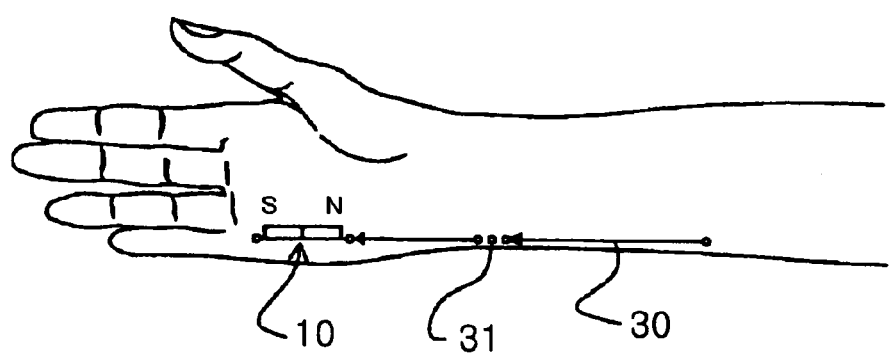
FIG. 4 shows an example in which a bar magnet is attached such that the direction of flow of a magnetic force is opposite to the direction of flow of the meridian system in the lung, heart constrictor and heart meridians.

On the contrary, as shown in FIG. 4, a bar magnet is attached such that the S pole is directed to the fingertips and the N pole is directed to the shoulder so that the direction of flow of a magnetic force is opposite to the direction of flow of the meridian system in the lung, heart constrictor and heart meridians, thereby inhibiting the meridian system by the magnetic force.

The method of modulating the flow of the meridian system using a small bar magnet according to the present invention will now be described in detail. However, the following methods are illustrative only and it is to be understood that it is no way limited to the disclosure of such illustrated methods but is capable of various modifications within the scope of the present invention.

(1) Attaching a Single Bar Magnet

A single bar magnet is attached to a part of pain or corresponding acupuncture point. According to the symptom, the bar magnet is attached such that the direction of an internal magnetic force of the magnet is the same as the direction of flow of the meridian system, thereby promoting the human meridian system, or the bar magnet is attached such that the direction of flow of a magnetic force is opposite to the direction of flow of the meridian system, thereby inhibiting the human meridian system.

(2) Attaching Bar Magnets in a Line

When parts of pain are developed in a long line on a body, bar magnets are attached lengthwise to the parts of pain at a constant interval, e.g., approximately 1 cm. Since a magnetic force of the magnet is applied lengthwise along the parts of pain, the effect of pain relief can be increased. In this case, the magnet is selectively attached by either a Bo (promotive) or Sa (inhibitive) method according to the symptoms such that the direction of flow of the magnetic force is the same as or opposite to the direction of flow of the meridian system.

(3) Attaching Two Magnets Side by Side

Two bar magnets are attached side by side at an interval of approximately 1 cm. When the two bar magnets are in the same direction, a relative great magnetic force is produced, so that the pain suppressing effect can be enhanced. On the contrary, two bar magnet may be attached in the opposite direction to each other, thereby appropriately modulating the effect.

(4) Attaching Bar Magnets Side by Side in Multiple Lines

This method is used when parts of pain are widespread in a stiff condition. In this case, tender points, oversensitive points or acupuncture points are detected and bar magnets are attached thereto side by side in more than 3 lines, usually in 4 to 5 lines such that the same poles of the bar magnets are disposed in the same direction. In the case where the diameter of a part of pain is greater than or equal to 5 cm, this method can be advantageously used to extend a magnetic field, thereby maximizing the therapeutic effect.

(5) Attaching Two Bar Magnets Together

Figure 5:
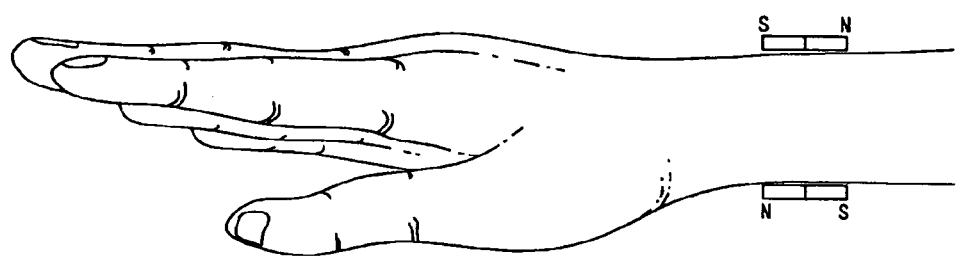
FIG. 5 shows an example in which bar magnets are put together around parts of pain.

A bar magnet is attached to a meridian at one side of a part of pain and another bar magnet is attached to a meridian at the opposite side of the part of pain, such that the direction of an internal magnetic force of the magnet is the same as or opposite to the direction of flow of the meridian system. For example, as shown in FIG. 5, a bar magnet is attached to Neiguan acupuncture point (PC06) such that the N pole of the bar magnet is directed to a fingertip, and another bar magnet is attached to Waiguan acupuncture point (SJ05) such that the N pole is directed to the elbow. This method is particularly effective for diseases in the circulation system, such as heart disease, hyperpiesia, stroke and the like, or diseases in the neck or shoulder.

(6) Attaching a Bar Magnet Followed by Tapping

After attaching a bar magnet in the above-described manner, the bar magnet is lightly tapped approximately 50 times, thereby increasing a magnetic field to offer bio-electricity, so that therapeutic effects can be enhanced.

(7) Hypodermic Implantation

Like in the case where a bar magnet is attached to the surface of the skin, a bar magnet is hypodermically implanted such that the direction of an internal magnetic force of the magnet is the same as or opposite to the direction of flow of the meridian system, thereby regulating the human meridian system. In detail, this method is performed by general implantation methods known in the medical and pharmaceutical fields, such as hypodermic implantation of an insulin pump. For example, the bar magnet according to the present invention can be put into an injection device in the form of a syringe and a piston of the syringe is pressed so that the bar magnet can be hypodermically inserted and implanted through a needle of the syringe. This method is particularly suitably adopted for chronic diseases such as hyperpiesia, stroke, heart disease, diabetes and the like.

According to the present invention, since the bar magnet used to modulate the meridian system is attached to the surface of the skin at a meridian or acupuncture point to be controlled, it is preferably a small bar magnet having a coercivity of 1000 gauss or greater. The bar magnet has a length of 3 cm or less, preferably 1 cm or less, and a thickness of 0.5 mm or less. More preferably, the bar magnet has a length of 5 mm or less and a thickness of 0.3 mm or less. As long as the coercivity of 1000 gauss or greater is maintained, the bar magnet is preferably as small as possible. The inventor of the present invention has developed and used a small bar magnet satisfying these requirements. Of course, it is possible to use a magnet having a length of 3 cm or greater in embodying the present invention with slight inconvenience of use.

In addition to the above-described bar magnet, any kind of a magnet that can make the direction of flow of an internal magnetic force be the same as or opposite to the direction of flow of the meridian system, for example, an electro-magnet. While the small bar magnet according to the present invention can be suitably used for ordinary people because of its portability, the electro-magnet can be effectively used for medical centers such as hospitals.

INDUSTRIAL APPLICABILITY

The present invention can replace acupuncture and/or moxibustion that have been conventionally used for modulating the human meridian system in the Oriental medical art. Unlike the conventional acupuncture or moxibustion, long-term treatment is allowed by performing hypodermic implantation of the bar magnet according to the present invention a single time. Also, the method of attaching the bar magnet to the surface of the skin according to the present invention can be used even by ordinary people who are not skillful practitioners, in a risk-free, safe and simple manner without causing pain to a body.

What is claimed is:

1. A method of modulating the human meridian system using a small bar magnet having a length of 3 cm or less and a coercivity of 1000 gauss or greater,
    wherein the small bar magnet is attached to the skin corresponding to at least two acupuncture points on the meridian line of the human body,
    wherein a first small bar magnet is attached to the skin corresponding to a first acupuncture point such that the direction of flow of a magnetic force of the first small bar magnet is the same as the direction of flow of the meridian system to promote the meridian system (Bo-method), or attached to the skin corresponding to the first acupuncture point such that the direction of flow of a magnetic force of the first small bar magnet is opposite to the direction of the meridian system to inhibit the meridian system (Sa-method), and
    a second small bar magnet is attached to the skin corresponding to a second acupuncture point such that the direction of flow of a magnetic force of the second small bar magnet is opposite to the direction of the meridian system to inhibit the meridian system (Sa-method) when the first small magnet bar is attached to the skin corresponding to a first acupuncture point such that the direction of flow of a magnetic force of the first small bar magnet is the same as the direction of flow of the meridian system to promote the meridian system (Bo-method), or attached to the skin corresponding to a second acupuncture point such that the direction of flow of a magnetic force of the second small bar magnet is the same as the direction of flow of the meridian system to promote the meridian system (Bo-method) when the first small magnet bar is attached to the skin corresponding to the first acupuncture point such that the direction of flow of a magnetic force of the first small magnet is opposite to the direction of the meridian system to inhibit the meridian system (Sa-method).

2. The method of claim 1, wherein the small bar magnet has a length of 1 cm or less and a thickness of 0.5 mm or less.

3. The method of claim 1, wherein the small bar magnet has a length of 5 mm or less and a thickness of 0.3 mm or less.

4. The method of claim 1, wherein the small bar magnet is attached to parts of pain in multiple lines in the same direction with or different directions from each other.

5. A method of modulating the human meridian system using a small bar magnet having a length of 3 cm or less and a coercivity of 1000 gauss or greater,
    wherein the small bar magnet is attached to the skin corresponding to at least two acupuncture points on the meridian line of the human body,
    wherein a first small bar magnet unit is attached to the skin corresponding to a first acupuncture point such that the direction of flow of a magnetic force of the first small bar magnet unit is the same as the direction of flow of the meridian system to promote the meridian system (Bo-method), or attached to the skin corresponding to the first acupuncture point such that the direction of flow of a magnetic force of the first small bar magnet unit is opposite to the direction of the meridian system to inhibit the meridian system (Sa-method), and
    a second small bar magnet unit is attached to the skin corresponding to a second acupuncture point such that the direction of flow of a magnetic force of the second small bar magnet unit is opposite to the direction of the meridian system to inhibit the meridian system (Sa-method) when the first small magnet bar is attached to the skin corresponding to a first acupuncture point such that the direction of flow of a magnetic force of the first small bar magnet unit is the same as the direction of flow of the meridian system to promote the meridian system (Bo-method), or attached to the skin corresponding to a second acupuncture point such that the direction of flow of a magnetic force of the second small bar magnet unit is the same as the direction of flow of the meridian system to promote the meridian system (Bo-method) when the first small magnet bar is attached to the skin corresponding to the first acupuncture point such that the direction of flow of a magnetic force of the first small magnet is opposite to the direction of the meridian system to inhibit the meridian system (Sa-method),
    wherein the first small bar magnet unit comprises a pair of small bar magnets which are positioned in the vicinity of the first acupuncture point and spaced apart from each other by a distance of 1 cm, and
    the second small bar magnet unit comprises a pair of small bar magnets which are positioned in the vicinity of the second acupuncture point and spaced apart from each other by a distance of 1 cm.

6. The method of claim 5, wherein the small bar magnet has a length of 1 cm or less and a thickness of 0.5 mm or less.

7. The method of claim 5, wherein the small bar magnet has a length of 5 mm or less and a thickness of 0.3 mm or less.

8. The method of claim 5, wherein the small bar magnet is attached to parts of pain in multiple lines in the same direction with or different directions from each other.

9. A method of modulating the human meridian system using a small bar magnet having a length of 3 cm or less and a coercivity of 1000 gauss or greater, wherein the small bar magnet is implanted into the skin corresponding to at least two acupuncture points on the meridian line of the human body, wherein a first small bar magnet is implanted into the skin corresponding to a first acupuncture point such that the direction of flow of a magnetic force of the first small bar magnet is the same as the direction of flow of the meridian system to promote the meridian system (Bo-method), or implanted into the skin corresponding to the first acupuncture point such that the direction of flow of a magnetic force of the first small bar magnet is opposite to the direction of the meridian system to inhibit the meridian system (Sa-method), and a second small bar magnet is implanted into the skin corresponding to a second acupuncture point such that the direction of flow of a magnetic force of the second small bar magnet is opposite to the direction of the meridian system to inhibit the meridian system (Sa-method) when the first small magnet bar is implanted into the skin corresponding to a first acupuncture point such that the direction of flow of a magnetic force of the first small bar magnet is the same as the direction of flow of the meridian system to promote the meridian system (Bo-method), or implanted into the skin corresponding to a second acupuncture point such that the direction of flow of a magnetic force of the second small bar magnet is the same as the direction of flow of the meridian system to promote the meridian system (Bo-method) when the first small magnet bar is implanted into the skin corresponding to the first acupuncture point such that the direction of flow of a magnetic force of the first small magnet is opposite to the direction of the meridian system to inhibit the meridian system (Sa-method).

10. The method of claim 9, wherein the small bar magnet has a length of 1 cm or less and a thickness of 0.5 mm or less.

11. The method of claim 9, wherein the small bar magnet has a length of 5 mm or less and a thickness of 0.3 mm or less.

12. The method of claim 9, wherein the small bar magnet is implanted into parts of pain in multiple lines in the same direction with or different directions from each other.

13. A method of modulating the human meridian system using a small bar magnet having a length of 3 cm or less and a coercivity of 1000 gauss or greater, wherein the small bar magnet is implanted into the skin corresponding to at least two acupuncture points on the meridian line of the human body, wherein a first small bar magnet unit is implanted into the skin corresponding to a first acupuncture point such that the direction of flow of a magnetic force of the first small bar magnet unit is the same as the direction of flow of the meridian system to promote the meridian system (Bo-method), or implanted into the skin corresponding to the first acupuncture point such that the direction of flow of a magnetic force of the first small bar magnet unit is opposite to the direction of the meridian system to inhibit the meridian system (Sa-method), and a second small bar magnet unit is implanted into the skin corresponding to a second acupuncture point such that the direction of flow of a magnetic force of the second small bar magnet unit is opposite to the direction of the meridian system to inhibit the meridian system (Sa-method) when the first small magnet bar is implanted into the skin corresponding to a first acupuncture point such that the direction of flow of a magnetic force of the first small bar magnet unit is the same as the direction of flow of the meridian system to promote the meridian system (Bo-method), or implanted into the skin corresponding to a second acupuncture point such that the direction of flow of a magnetic force of the second small bar magnet unit is the same as the direction of flow of the meridian system to promote the meridian system (Bo-method) when the first small magnet bar is implanted into the skin corresponding to the first acupuncture point such that the direction of flow of a magnetic force of the first small magnet is opposite to the direction of the meridian system to inhibit the meridian system (Sa-method), wherein the first small bar magnet unit comprises a pair of small bar magnets which are positioned in the vicinity of the first acupuncture point and spaced apart from each other by a distance of 1 cm, and the second small bar magnet unit comprises a pair of small bar magnets which are positioned in the vicinity of the second acupuncture point and spaced apart from each other by a distance of 1 cm.

14. The method of claim 13, wherein the small bar magnet has a length of 1 cm or less and a thickness of 0.5 mm or less.

15. The method of claim 13, wherein the small bar magnet has a length of 5 mm or less and a thickness of 0.3 mm or less.

16. The method of claim 13, wherein the small bar magnet is implanted into parts of pain in multiple lines in the same direction with or different directions from each other.

* * * * *